(12) United States Patent
Richardson et al.

(10) Patent No.: US 7,252,706 B2
(45) Date of Patent: Aug. 7, 2007

(54) INHIBITION OF CALCIUM AND MAGNESIUM PRECIPITATION FROM WOOD PRESERVATIVES

(75) Inventors: H. Wayne Richardson, Sumter, SC (US); Gang Zhao, Sumter, SC (US)

(73) Assignee: Phibro-Tech, Inc., Fort Lee, NJ (US)

( * ) Notice: Subject to any disclaimer, the term of this patent is extended or adjusted under 35 U.S.C. 154(b) by 0 days.

(21) Appl. No.: 10/545,605

(22) PCT Filed: Jun. 17, 2004

(86) PCT No.: PCT/US2004/019646

§ 371 (c)(1),
(2), (4) Date: Aug. 16, 2005

(87) PCT Pub. No.: WO2004/113038

PCT Pub. Date: Dec. 29, 2004

(65) Prior Publication Data

US 2006/0162611 A1    Jul. 27, 2006

Related U.S. Application Data

(60) Provisional application No. 60/478,820, filed on Jun. 17, 2003, provisional application No. 60/478,827, filed on Jun. 17, 2003.

(51) Int. Cl.
  B27K 3/22  (2006.01)
  B27K 3/24  (2006.01)
  A01N 57/00  (2006.01)
  A01N 59/20  (2006.01)
  A01N 59/26  (2006.01)

(52) U.S. Cl. .................. 106/18.31; 106/18.32; 424/638; 424/682; 424/722; 514/75; 514/141; 514/500

(58) Field of Classification Search ............ 106/18.31, 106/18.32; 424/604, 638, 722, 682; 514/141, 514/75, 500
See application file for complete search history.

(56) References Cited

U.S. PATENT DOCUMENTS

| | | | | |
|---|---|---|---|---|
| 3,475,393 A | * | 10/1969 | Langguth et al. ........... 205/271 |
| 3,844,760 A | * | 10/1974 | Nelson ........................ 504/152 |
| 4,510,074 A | * | 4/1985 | Nakai et al. .............. 252/400.2 |
| 4,737,491 A | * | 4/1988 | Leppavuori et al. ...... 424/78.18 |
| 4,933,051 A | * | 6/1990 | Kline ........................... 205/295 |
| 5,186,947 A | * | 2/1993 | Goettsche et al. .......... 424/638 |
| 5,874,025 A | * | 2/1999 | Heuer et al. ................. 252/383 |
| 6,375,727 B1 | * | 4/2002 | Walker ..................... 106/18.32 |
| 2004/0258768 A1 | * | 12/2004 | Richardson et al. ........ 424/630 |
| 2006/0062926 A1 | * | 3/2006 | Richardson et al. ........ 427/440 |
| 2006/0075923 A1 | * | 4/2006 | Richardson ............... 106/18.26 |
| 2006/0078686 A1 | * | 4/2006 | Hodge et al. ................ 427/440 |

FOREIGN PATENT DOCUMENTS

| | | | | |
|---|---|---|---|---|
| GB | 1238469 A | * | 7/1971 |
| GB | 2177003 A | * | 1/1987 |
| JP | 63-238865 A | * | 10/1988 |
| SU | 617451 A | * | 7/1978 |

OTHER PUBLICATIONS

Derwent Abstract No. 1982-07499E, abstract of Soviet Union Patent Specification No. SU821440B (Apr. 1981).*

* cited by examiner

*Primary Examiner*—Anthony J. Green
(74) *Attorney, Agent, or Firm*—Morgan, Lewis & Bockius LLP

(57) ABSTRACT

A wood preservative that contains a copper salt complex and a precipitation inhibitor is provided. The wood preservative may contain copper carbonate, an alkanolamine such as monoethanolamine and precipitation inhibitor such as a phosphonate or ethylene diamine compound. Also provided is a method of using the wood preservative.

17 Claims, No Drawings

INHIBITION OF CALCIUM AND MAGNESIUM PRECIPITATION FROM WOOD PRESERVATIVES

RELATED APPLICATIONS

The present application is a U.S. National Phase Application of International Application PCT/US2004/019646 (filed Jun. 17, 2004) which claims the benefit of U.S. Provisional Application No. 60/478,820 (filed Jun. 17, 2003) and U.S. Provisional Application No. 60/478,827 (filed Jun. 17, 2003), all of which are herein incorporated by reference in their entirety.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

SEQUENCE LISTING

Not Applicable.

FIELD OF THE INVENTION

The invention relates to the use of compounds to prevent scale formation in wood preservative formulations formed by mixing a concentrated aqueous copper-amine complex solution with available water. More particularly, the invention relates to the use of specific phosphonate-containing scale inhibitors to reduce or eliminate calcium and magnesium carbonate precipitation during mixing of a concentrated aqueous copper-amine complex solution with available water.

BACKGROUND OF THE INVENTION

Wood contacting the ground or above ground wood that often gets wet, will typically be attacked by decay fungi and insects. With the exception of naturally durable species, such as cedar or redwood, wood in such applications is treated with a wood preservative, thereby increasing the longevity. The primary preserved wood product has historically been southern pine lumber treated with chromated copper arsenate (CCA). Most of this treated lumber was used for decks, fencing, and landscape timbers. There has recently been raised concerns about the safety and health effects of CCA as a wood preservative, primarily relating to the arsenic content but also to the chromium content. In 2003/2004, due in part to regulatory guidelines and to concerns about safety, there has been a substantial cessation of use of CCA-treated products. As a result, new wood preservatives have been developed. The new generation of copper containing wood preservatives uses a form of copper that is soluble. Known preservatives include copper alkanolamine complexes, copper polyaspartic acid complex, alkaline copper quaternary, copper azole, copper boron azole, ammoniacal copper citrate, copper bis(dimethyldithiocarbamate), copper citrate, and the copper ethanolamine carbonate. While the name might not suggest it, all have a nitrogen base that complexes the copper, e.g., ammoniacal copper, monoethanolamine copper, diethyleneamine copper, and so forth, and most formulations have carbonate ions to stabilize the complexes. When these formulations contact water having alkaline earth ions, e.g., calcium and magnesium, scale will form.

The problem of precipitate formation (scaling) is not unique to wood preservatives. Manufacturing processes utilizing water, water treatment facilities, households, among others have also been faced with the problem of scale formation. A typical solution to scale formation has been to employ a chemical agent and an absorbent material or surfactant to prevent or remedy scale deposits. For instance, U.S. Pat. No. 6,645,384 to Richardson et al. discloses the use of 2 phosphonobutane 1,2,4 tricarboxylic acid and a quad polymer having a polyacrylate/methacrylate base and 6 wt % sulfonated monomers (allyloxybenzenesulfonic acid and methallyl sulfonic acid) to prevent accumulation of mineral scale and corrosion. Similarly, U.S. Pat. No. 6,641,740 to Cornelius et al. discloses use of algins, polysaccharides isolated from algae, to remove scale deposits. Yet another example is U.S. Pat. No. 3,518,204 to Hansen et al. which discloses a method to control the rate of scale formation with compounds such as triglycollamic acid and polyacrylamide. Another approach has been to introduce a scale formation inhibitor, such as monofluorophosphate salts, as disclosed in U.S. Pat. No. 5,182,028 to Boffardi et al. While these approaches are optimal in their respective fields of use, they do not allow for sufficient precipitate inhibition in the field of wood preservatives.

Wood preservatives commonly comprise a second biocide that is efficacious against the copper tolerant organisms and other particularly troublesome species. The second biocide is often composed of a triazole group or a quaternary amine group or a nitroso-amine group. In practice the principal criteria for commercial acceptance, assuming treatment efficacy, is cost. Of the many compositions listed above, only a few soluble copper containing wood preservatives have found commercial acceptance, and each comprises either a copper monoethanolamine carbonate complex or an ammoniacal copper carbonate complex.

Typically, the wood preservatives are shipped and stored in concentrated form. The concentrate is therefore diluted with available water before use. The diluent water is usually ordinary municipal water or even stream water, both of which may contain calcium and/or magnesium. If the diluted wood preservatives contain calcium and magnesium above the solubility level of their respective carbonates, precipitates will form. Such precipitates are known as scales. In general scale formation occurs when solubility of a particular salt is exceeded.

Such precipitates (scales) are considered objectionable and problematic, as they can cause a stain on the wood (which would often be colored by the copper) and/or cause plugging of the wood during a pressure injection treatment. To prevent plugging and staining, scales and other presipitates are usually filtered out of the copper containing solution, a step that may add significant cost to the wood treatment process. Another problem with scale that can not be addressed by filtering is that scale can act like a sponge to strip an inordinate amount of copper and more particularly of the inorganic biocides from the wood preservation composition.

A method of preventing scale formation is needed.

SUMMARY OF THE INVENTION

The present invention relates to aqueous copper-amine-based wood preservatives that contain a precipitation inhibitor and methods of use thereof. The problem of preventing calcium/magnesium carbonate precipitation in aqueous wood preservative solutions is much more difficult than in most aqueous systems using a scale inhibitor to inhibit scale. Most aqueous systems operate with an extremely small concentration of carbonate and with a moderate concentration of calcium and magnesium. In contrast, in the manufacture of wood preservative formulations, compositions are encountered that have extremely high levels of carbonate and a moderate concentration of calcium and magnesium.

These wood preservative concentrates all comprise an aqueous base containing complexed copper as a principal ingredient, where the complexing agent is an amine, typically ammonia, monoethanolamine, ethylenediamine, or a mixture thereof. Other less-used formulations may include diethanolamine or mixtures of monoethanolamine and ammonia, for example. These copper complexes are prepared in centralized locations, using for example the process disclosed in U.S. Pat. No. 6,646,147, the disclosure of which is incorporated herein by reference thereto. Precipitation inhibitors of the invention should completely inhibit precipitation of calcium and magnesium carbonates in the concentrates. By "concentrate" it is meant that the concentration of copper present in the concentrate is greater than a concentration of copper present in the wood preservative material as ready for use to preserve wood or wood products, such as by pressure injection therein. An exemplary aqueous concentrate contains between 8 and 16% by weight of dissolved copper, and has a pH between 8.5 and 13, more typically between 9.5 and 11. The pH is reduced from about 13 by the addition of acid, typically carbonic acid, and the carbonate ions stabilize the copper-amine complexes. As a result, these concentrates typically comprise between 3 and 12% by weight of carbonate ions to stabilize the complexes.

Concentrates are at least 5 times, for example, at least about 15 times, for example about 20 times more concentrated than the wood preservative as generally applied to wood or wood products. On site, the wood preservative concentrate is diluted with water prior to treatment of the wood. Generally, a composition comprising between 0.25% and 2% by weight copper is injected into wood during the wood preservation process, so the dilution may range from 1 part concentrate to 3 parts water to 1 part concentrate to 64 parts water. The very high carbonate concentrations in the concentrate, however, make even fairly fresh water form scale. Water used to prepare a wood preservative does not have to be hard in order to yield precipitates. In one study it has been observed that precipitates are visible within 24 hours from waters that contain only about 100 ppm hardness, which is considered soft water.

Some wood preservative users do not use the aqueous concentrates, but rather formulate a complexed-copper wood preservative formulation at or near the site of end use, using for example commodity items such as basic copper carbonate in the formulation. This basic copper carbonate is a solid, and it typically comprises a level of calcium and magnesium. This calcium and magnesium contaminant will be added to the calcium and magnesium in the diluent water, both of which will react with available carbonate to form scale.

In view of the large excess of carbonate that typically is found, the inhibition effort beneficially focuses on the calcium and magnesium (and strontium, if present). While it may seem trivial to simply add a large excess of chelators such as EDTA to a system to chelate any potential calcium and magnesium in the waters during mixing, such an approach is not practicable. The concentrate comprises a large quantity of copper, where the copper is complexed by the interactions of the copper and between 3 and 4 amine molecules, e.g., ammonia or monoethanolamine. Strong chelators in the concentrate will simply strip copper from the complexes during shipment and storage of the concentrate, and/or during the dilution process. The strong chelators will then be exhausted and will not have capacity to bind with the calcium, magnesium, and/or strontium. Preferred precipitation inhibitors should complex selectively with calcium, magnesium, and/or strontium as compared to copper, and thus prevent the precipitation of alkaline earth carbonates (such as e.g. calcium carbonate) from aqueous solution.

Applicant have found that certain phosphonate compounds, especially those having a plurality of phosphonate $PO_3H_2$ groups separated by two or three atoms, typically carbon, could solubilize calcium and magnesium ions in a wood preservative composition. The mechanism is most likely that the compounds complex the alkaline earth ions.

Preferred compounds have a plurality of phosphonate moieties, where the phosphonate moieties are separated by two atoms in a molecule—preferably two carbons, and less preferably a carbon and a nitrogen, for example. Molecules having three atoms between phosphonate moieties are useful but are less preferred. Inhibitors not containing a nitrogen in the 2-4 atom chain between the phosphonate moieties are preferred over inhibitors that do contain a nitrogen in the 2-4 atom chain between the phosphonate moieties. A preferred variant comprises an inhibitor wherein at least one, but not all, phosphonate moieties are replaced by a carboxylate moiety.

The most common example, and the most effective inhibitor having these properties, is hydroxyethylidene diphosphonic acid (HEDP), also called (2-Hydroxy-2-phosphonoethyl)-phosphonic acid. One mole of HEDP, having two phosphonate moieties per molecule, can apparently complex and solubilize about 1.5 moles calcium and 2 moles of magnesium in a copper- and carbonate-containing solution that has an excess of calcium and magnesium ions. In a copper-monoethanolamine-carbonate concentrate having excess calcium (but no magnesium), a mole of HEDP was able to solubilize about 4 moles of calcium. HEDP is preferred because it is effective and because it has a reduced tendency to adhere onto existing scale where it will not be effective, as compared to other inhibitor molecules discussed below.

The inhibitor molecule can have a phosphonate moiety and one or more carboxylate moieties, again advantageously separated by two atoms. For example, 2-phosphonobutane-1,2,4-tricarboxylic acid (PBTC) has a phosphonate moiety separated from a first carboxylate by a single carbon, from a second carboxylate by two carbons, and from a third carboxylate by three carbons. One mole of PBTC, having one phosphonate and three carboxylate moieties per molecule, can apparently complex and solubilize about 1.5 moles calcium and 0.6 moles of magnesium in a copper- and carbonate-containing solution that has an excess of calcium and magnesium ions. We believe this compound has a moderately higher tendency to plate onto existing scale, and therefore to be removed from the solution, than does HEDP. Further, this compound has a smaller solubilizing effect on magnesium (per mole) than does HEDP.

Other useful inhibitors are compounds that comprise three atom separation between phosphonate moieties, e.g., (phosphonate)-C—N—C-(phosphonate). Examples include (Phosphonomethyl-amino)-methyl-phosphonic acid and the common diethylenetriamine-pentamethylenephosphonic acid (DTPMP). One mole of DTPMP, having five phosphonate moieties per molecule, can apparently complex and solubilize about 1.6 moles calcium and 1 mole of magnesium in a copper- and carbonate-containing solution that has an excess of calcium and magnesium ions. This compound, however, is less preferred because it can cost two to three times as much per mole as HEDP costs. We also believe this compound has a higher tendency to plate onto existing scale, and therefore to be removed from the solution, than does HEDP. Additionally, a close analogue of DTPA is amino-tri (methylenephosphonic) acid (ATMP), which has three phosphonates, each separated by three atoms —C—N—C—, but where the N is shared by all three phosphonate moieties. ATMP surprisingly had no beneficial effect.

Similarly, ethylenediaminetetramethylene phosphonic acid (EDTMP), having two sets of phosphonate moieties each separated by a three atom C—N—C group, was found to be marginally effective. Each mole of EDTMP seems to be capable of solubilizing one mole of calcium.

Because there is always some loss of inhibitor due to plating out, the concentrate and the diluted wood treatment solution should contain a minimum value of inhibitor, to anticipate probable loss of inhibitor. For HEDP, the minimum is estimated to be about 20 mg/L. For PBTC and for DTPMP, the minimum is estimated to be over 100 mg/L. The use of EDTMP is discouraged.

A variety of other potential scale inhibitors were screened. Citric acid, borogluconate, Di-(2-ethylhexyl) phosphoric acid (DEHPA), and o-phosphorylethanolamine were found to be ineffective. Ethylenediaminetetramethylene phosphonic acid was marginally effective, and HEDP was very effective.

The preferred phosphonate-based inhibitors can solubilize at least 3 moles calcium and/or magnesium, so as to prevent precipitation in the concentrate. A concentrate should have at least 0.33 moles inhibitor (if HEDP is used) or at least 0.5 moles of inhibitor (if PBTC is used). One aspect of the invention is a wood preservative concentrate comprising a phosphonate-based inhibitor of this invention in an amount to provide more than 0.3 moles, preferably more than 0.5 moles, per mole of alkaline earth ions (i.e., hardness) in the concentrate. For example, if a concentrate is prepared and the average hardness is 0.4 mmoles/L but ranges day by day between 0.3 mmoles/L and 0.5 mmoles/L, then the minimum inhibitor concentration is advantageously based on the 0.5 mmole/L value. A concentrate having more than about 0.15 mmoles/L, for example about 0.2 mmoles/L of HEDP would be adequately protected against precipitation in the concentrate. If PBTC is used, a concentrate having more than about 0.25 mmoles/L, for example about 0.3 mmoles/L of PBTC would be adequately protected against precipitation in the concentrate.

Generally, the concentration of alkaline earth ions, e.g., calcium, magnesium, and strontium, is called "hardness." Hardness can be reported as mg/L as calcium, mg/L as calcium carbonate, or as millimoles per liter of these compounds. A preferred wood preservative concentrate will comprise at least 0.3 millimoles, preferably at least 0.5 millimoles, of a phosphonate-based inhibitor per millimole of hardness, wherein the inhibitor is intended to prevent scale deposition in the concentrate.

A second aspect of the invention is a wood preservative concentrate comprising a phosphonate-based inhibitor of this invention in an amount 0.3 times or more, preferably more than 0.5 times, the moles of alkaline earth ions in the concentrate and in the expected dilution water, i.e., the hardness in the expected wood treatment composition. For example, if a concentrate containing 100 milligrams hardness as calcium (2.5 millimoles as Ca/L) is normally diluted 9:1 with water, and the manufacturer states the diluent water should have a hardness less than 200 mg/L as calcium (5 millimoles as Ca/L) or be otherwise treated, then the concentrate should have an inhibitor concentration sufficient to complex the hardness in both the concentrate and in the water. This amount is easily computed as follows:

mmoles inhibitor/L=(9 L*5 mmoles hardness/L+1 L*2.5 mmoles hardness/L)×0.3 mmoles inhibitor/mmole hardness=14.3 mmoles/L of inhibitor.

The amount of HEDP inhibitor in the concentrate, e.g., greater than 14.3 mmoles/L, should prevent precipitation in a wood treatment composition formed by mixing the concentrate 9 to 1 with water, where the water has a hardness of 5 mmoles/L or less.

The absolute amount of inhibitor in a concentrate can vary, as the manufacturer selects the inhibitor or inhibitors to use, and projects the dilution rate and hardness in the diluent water. A maximum expected dilution of a concentrate under normal conditions is 50 to 1. A maximum hardness in the diluent water is about 1000 mg hardness/L as calcium, or about 25 mmoles/L. The hardness in the concentrate is negligible. Therefore, if HEDP is used, a concentration of more that about 50 times 25 times 0.3, or more than 375 mmoles/L, should prevent precipitation under any anticipated field use.

A concentrate should generally contain between 14.3 mmoles and 375 mmoles of HEDP/L to prevent precipitation of scale during preparation and use of wood preservative compositions. However, high amounts of phosphonate-based inhibitor in a concentrate are very expensive, and it is generally not needed for most dilution factors and for softer waters. A concentrate can reasonably contain between 20 and 100 mmoles/L of HEDP, or between 33 and 170 mmoles/L of PBTC or DTPMP. A concentrate having 10-50 mmoles, alternately 51-100 mmoles, alternately 101-200 mmoles, alternately 201-400 mmoles, alternately 401-700 mmoles, alternately 251-400 mmoles of PBTC and/or DTPMP /L, are envisioned in this invention. A concentrate having 10-20 mmoles HEDP/L, alternately 21-50 mmoles HEDP/L, alternately 51-100 mmoles HEDP/L, alternately 101-170 mmoles HEDP/L, alternately 171-250 mmoles HEDP/L, alternately 251-400 mmoles HEDP/L are envisioned in this invention. Mixtures of inhibitors are preferred, as concentrates may have more inhibitor than can readily be solubilized therein. A concentrate comprising HEDP and DTPMP would be useful, where the recommended amounts can be readily calculated by one of ordinary skill in the art having benefit of this disclosure.

One aspect of the invention relates to a water soluble wood preservative comprising an aqueous solution of a copper salt, one or more alkaline earth metal ions, and a phosphonate-based complexing agent of this invention, wherein the molar ratio of the inhibitor to the alkaline earth metal ions is between 1:3 and 4:1, alternatively between about 1:2 and 2, alternatively between 1:1.5 and 1.5:1. Another aspect of the invention is a method of treatment of wood with a wood preservative comprising the steps of: providing a water soluble wood preservative described above, and injecting the preservative into wood.

Similar calculations are readily made for solid materials, such as basic copper carbonate. If a basic copper carbonate salt has 4 g hardness as Ca per kg material, and 1 kg of basic copper carbonate is diluted with 100 kg of water having a hardness of 200 mg/L as Ca, then a kg of basic copper carbonate should contain sufficient inhibitor to complex about 0.6 moles of hardness. Such a composition would comprise more than 0.18 moles HEDP per kg, or more than 0.3 moles of PBTC and/or DTPMP per kg of basic copper carbonate. Representative soluble copper salts, especially copper carbonates and/or basic copper carbonates, should comprise between about 0.1 to about 4 mole HEDP per kg, for example 0.2 to 1 mole HEDP/kg, to prevent precipitation under most conditions of use. Representative soluble copper salts, especially copper carbonates and/or basic copper carbonates, should comprise between about 0.17 to about 7 mole PBTC and/or DTPMP/kg, for example 0.3 to 1.7 mole PBTC and/or DTPMP/kg, to prevent precipitation under most conditions of use.

Of course, lesser amounts of inhibitors may be used, such as 30% less than the recommended amounts of inhibitor, if an operator believes that elimination of scale is not justified, but would rather just reduce the amount of scale to reduce operational problems.

The copper-based wood preservatives comprise one or more organic biocides. Generally, the concentration of biocides is not significant. However, biocides can solubilize alkaline earth metal ions. In one embodiment, the precipitation agent is a triazole compound, such as N-alkylated tolyltriazole.

DETAILED DESCRIPTION OF THE PREFERRED EMBODIMENTS

As used hereinafter, the term "wood preservative" shall refer to a material useful for preserving wood and/or wood products. Furthermore, the term complexing material is synonymous with the term complexing agent.

A biocide solution, such as a wood preservative, may be prepared by combining a copper compound and an amine, such as, e.g., monoethanolamine, to form a mixture. The resulting mixture comprises a complex comprising copper and an amine. The mixture may also include water, which may include impurities that give rise to the precipitation problem.

One aspect of the present invention is related to minimizing and or inhibiting precipitation of solids from wood treating materials, such as preservatives for wood and wood products. Wood and wood products treated with wood treating materials of the invention may be free of stains associated with precipitation of materials such as calcium and magnesium. In any event, wood and wood products treated with wood treating materials of the invention exhibit reduced staining from such precipitation as compared to wood preservative products not containing precipitation inhibitors.

The material useful for preserving wood and/or wood products (referred to herein as a "wood preservative") comprises: a (1) soluble copper salt and complexing material/agent and; (2) a precipitation inhibitor. In one embodiment, the wood preservative comprises copper carbonate and an amine as the complexing material/agent. For example, the wood preservative may comprise at least one of copper monoethanolamine, copper diethanolamine and copper ethylenediamine. Other copper-amine and diamine-copper complexes are also suitable. In one embodiment, the wood preservative comprises copper carbonate and monoethanolamine. In an alternate embodiment, the wood preservative comprises copper carbonate and diethanolamine. In another embodiment, the wood preservative comprises copper carbonate and isopropanolamine. The copper salt and complexing agent may also comprise copper polyaspartic acid complex, alkaline copper quaternary, copper azole, copper boron azole, ammoniacal copper citrate, copper bis(dimethyldithiocarbamate), copper citrate, and the copper ethanolamine carbonate.

The wood preservative may comprise a flowable material, such as at least one of a liquid, a solution, an emulsion, and a slurry. For example, the wood preservative may comprise an aqueous solution comprising at least one of copper monoethanolamine, copper 2-ethanolamine and copper ethylenediamine. The wood preservative may comprise a carbonate, such as a carbonate of the copper amine.

The wood preservative further comprises one or more precipitation inhibitors, which inhibit the precipitation (scaling) of one or more materials from the wood preservative. Such materials may be ionic species commonly associated with hard water. The precipitation inhibitor may be an alkaline earth precipitation inhibitor that inhibits precipitation of one or more alkaline earths. Particularly, the precipitation inhibitor may inhibit the precipitation of at least one of calcium and magnesium. The precipitation inhibitors may inhibit precipitation of a material by complexing or chelating with the material. Additionally, the precipitation inhibitor may enhance the solubility of one or more materials in the wood preservative.

The precipitation inhibitor may be present in a concentrated wood preservative, such as one suitable for shipping and benefiting from dilution, to prepare a wood preservative. The precipitation inhibitor may be present, alternatively or in addition, in a wood preservative having a copper concentration suitable for application to wood or wood products.

Precipitation of alkaline earths may be inhibited in wood preservative materials comprising standard hard water. Precipitation may be inhibited in wood preservative materials comprising as much as 100 ppm alkaline earths, for example as much as 150 ppm, as much as 200 ppm, as much as 300 ppm alkaline earths, or as much as 400 ppm alkaline earths. The precipitation inhibitors may optimally be present in molar ratio of inhibitor to Ca (e.g. Ca to HEDP) of approximately 1:3, or 1:2. In a preferred embodiment, the precipitation inhibitor is HEDP and it is present in a molar ratio from about 1:3 to about 1:2.

In one embodiment, the precipitation inhibitor may comprise a phosphonate based compound, such as a phosphonate that complexes at least one of calcium and magnesium. Among suitable phosphonates are those having one or more —C—PO$_3$—H$_2$ groups. A suitable phosphonate may be synthesized from phosphorous acid by reaction with formaldehyde and either ammonia or amines. A wood preservative of the invention may include at least one of an amino-tris(methylenephosphonic acid), an ethylenediamine-tetra (methylenephosphonic acid), a hexamethylenediamine-tetra (methylenephosphonic acid), a diethylenetriamine-penta (methylenephosphonic acid), and a 1-hydroxyethane-diphosphonic acid.

In an alternate embodiment, the precipitation inhibitor comprises at least one and preferably at least two phosphonic groups. The precipitation inhibitor may comprise a phosphonic acid or salt of a phosphonic acid. The precipitation inhibitor may comprise at least one of a hydroxyethylidene-diphosphonic acid and an aceto-diphosphonic acid. The precipitation inhibitor may also comprise amino-tris (methylenephosphonic acid) (ATMP).

The precipitation inhibitor may be a complexing agent. Suitable complexing agents include ethylenediamine and organic dicarboxylic acids. Examples of suitable complexing agents include but are not limited, e.g., ethylenediamine-tetraacetic acid (EDTA), diethylenetriaminepentacetic acid (DPTA), t-butyl catechol, pyrocatechol, gallic acid, citric acid, oxalic acid, glycolyic acid, tartaric acid and lactic acid. In one embodiment, the precipitation inhibitor comprises at least one ethylene diamine compound, such as an ethylenediamine-tetramethylene compound or ethylenediaminetetracetate compound. An acid, such as a phosphonic or acetic acid, of the ethylenediamine compound may be used. Salts of the ethylenediamine compound may also be used. In an alternate embodiment, the precipitation inhibitor comprises ammonium salts of ethylenediaminetetraacetic acid (EDTA).

The wood preservative may further comprise an additional material having a wood preservative effect. For example, the wood preservative may comprise at least one of a triazole group, a quaternary amine group, or a nitrosoamine group. The additional material may be a biocide. In another embodiment, the wood preservative may comprise a triazole compound and/or derivative, such as N-alkylated tolytriazole.

In another embodiment of the invention, copper carbonate and an amine are combined in the presence of a precipitation inhibitor, which may be a complexing agent. The precipitation inhibitor may be added prior to combining the copper carbonate and amine or to the mixture formed by the combination. Preferably, the combined product may be used without filtration as a wood preservative. An exemplary precipitation inhibitor comprises the phosphonate compounds described herein.

The wood preservative according to the instant disclosure is suitable for use with woods that are commonly treated with preservatives, such as southern pine. Upon treatment, such wood becomes impregnated with the wood preservative. Another aspect of the present invention relates to a method of treating wood with a wood preservative. The method comprises diluting a wood preservative comprising a copper salt, precipitation inhibitor, and amine with water and then treating a wood surface with the wood preservative. The method is particularly useful in conventional pressure vessels known in the art.

The precipitation inhibitor may also or alternatively result in the utilization of a greater fraction of copper based preservative and any organic biocide present in the wood preservative material. For example, at certain levels of calcium and magnesium, some of copper (an active biocide) is removed from the solution by the precipitating alkaline earths. Additionally or alternatively, the precipitating compounds may remove emulsified organic biocides from solution by adsorption on the precipitate. This may lead to losses of biocide from the wood preservative material. Furthermore, disposal and/or treatment of the precipitate is needed. By inhibiting precipitation in wood preservative materials, the present invention reduces these problems.

EXAMPLE 1

Six precipitation inhibitors were screened for ability to inhibit precipitation of calcium in a material comprising copper and an amine. A standard copper monoethanolamine carbonate (CMC) solution was used as the copper and amine comprising material.

About 400 ppm of each precipitation inhibitor was added to standard CMC solutions and mixed well. Subsequently, about 315 ppm calcium was added to the solutions. After mixing and settling over night (24 hrs), each solution was filtered and analyzed to determine the amount of soluble calcium present. The results are given below.

| Sample ID | Description | | Soluble Ca in CMC, ppm |
|---|---|---|---|
| 1 - | Control 1 | Original CMC | 16.5 |
| 2 - | Control 2 | Added 315 ppm Ca only | 85 |
| 3 - | Citric acid | Ca + 400 ppm citric acid | 91 |
| 4 - | Borogluconate (BG) | Ca + 400 ppm BG | 89 |
| 5 - | Hydroxyethylidene-diphosphonic acid (HEDP) | Ca + 384 ppm HEDP | 380 |
| 6 - | Ethylenediamine-tetra(methylenephosphonic acid)(EDTMP) | Ca + 400 ppm EDTMPS | 122 |
| 7. | Di-(2-ethylhexyl)phosphonic acid (DEHPA) | Ca + 500 ppm DEHPA | 87 |
| 8 - | O-phosphorylethanolamine | Ca + 400 ppm | 85 |

EXAMPLE 2

In a second study, the amount of soluble calcium present in CMC solutions comprising 400 ppm calcium and different amounts of hydroxyethylidene-diphosphonic acid (HEDP) was determined. The second study was carried out in fashion similar to that of the first study except that 400 ppm Ca was added to each CMC solution and different amounts of HEDP were studied. Additionally, the solutions were allowed to settle for 48 hours prior to determining the soluble calcium concentration. The results are given below.

| Sample ID | Description | HEDP, ppm | Soluble Ca, ppm |
|---|---|---|---|
| Control | 400 ppm Ca added | 0 | 178 |
| 1 | 400 ppm Ca added | 35 | 138 |
| 2 | 400 ppm Ca added | 70 | 149 |
| 3 | 400 ppm Ca added | 140 | 309 |
| 4 | 400 ppm Ca added | 210 | 339 |
| 5 | 400 ppm Ca added | 280 | 364 |

The slope of a linear least square analysis of the above date indicates that about 0.87 units of calcium is solublized with addition of each unit of HEDP.

EXAMPLE 3 AND 4

Example 3 and 4 are studies regarding the effectiveness of phosphonate containing BCC (basic copper carbonate) in producing low residue CMC product solutions. These studies focused on mixing phosphonates to the post-precipitated BCC. The effectiveness of these complexers was studied on both wet and dried BCC. In all studies, phosphonates were initially diluted to contain 1-6% active ingredient and applied to the wet BCC cake. The cakes were either dried in the lab oven (56° C.) over night or used as wet for the following studies.

When the solubility of calcium and magnesium were investigated in these studies, the following procedure was followed. In each test (unless otherwise stated), about 24.2 g treated BCC (dry basis) was mixed with 59 g MEA (99%) and DI water to a total weight of 145 g (120 ml). This composition will imitate that of a residue from a test solution containing about 9.2% copper, 40% monoethanolamine (MEA) and 3.3% $CO_2$. After dissolving, each unit of added phosphonate to the dry BCC (or wet BCC on dry basis)

would become 6.0 unit per liter volume in the solution. The sample was mixed on stir plates (9×multiple stations) under good agitation overnight (24 hours) unless otherwise stated. A small portion of the solution was then filtered with a Gooch funnel using Whatman 24-mm GF/A (1.6 micron pore size) glass fiber filter paper. The filtered solution was analyzed for calcium and magnesium by flame atomic absorption spectrometry (flame AA).

The table below lists the physical properties of the exemplary phosphonates used in the studies of Example 3 and 4.

| Abbreviation | Chemical Name | Formula | MW | Equivalent weight per phosphorous |
|---|---|---|---|---|
| HEDP | Hydroxyethylidene-diphosphonic acid | $C_2H_8O_7P_2$ | 206 | 103 |
| ATMP | Amino-tris(methylene phosphonic acid) | $C_3H_{12}N_3O_9P_3$ | 299 | 100 |
| PBTC | 2-Phosphonobutane-1,2,4-tricarboxylic acid | $C_7H_{11}O_9P$ | 270 | 270 |
| DTPMP | Diethylenetriamine penta(methylene phosphonic acid) | $C_9H_{28}N_3O_{15}P_5$ | 573 | 115 |

EXAMPLE 3

In a third study, the effectiveness of calcium complexers among the above phosphonates (HEDP, ATMP, PBTC, and DTPMP) was determined. Dried BCC doped with different levels of phosphonates were studied. The BCC for the following studies was freshly prepared in the lab and contained 1800 ppm calcium and 596 ppm magnesium, respectively. The soluble calcium and magnesium concentrations are listed in the table below.

| Phosphonate | Addition Rate, mg/L | Soluble Calcium, mg/L | Soluble Magnesium, mg/L |
|---|---|---|---|
| Control | 0 | 59.2 | 41 |
| HEDP | 140 | 113.2 | 56.4 |
| HEDP | 558 | 301 | 120 |
| ATMP | 140 | 47.6 | 55.2 |
| ATMP | 558 | 58.9 | 46.3 |
| PBTC | 140 | 34.2 | 46.5 |
| PBTC | 558 | 197.6 | 71 |
| DTPMP | 140 | 34.2 | 43.5 |
| DTPMP | 558 | 120 | 66 |

Surprisingly, the addition of phosphates at a low 140 mg/L level in CMC resulted in mostly negative effect on the solubility of calcium in such solutions. While the solubility of the magnesium increased slightly at the same conditions. However, HEDP showed a significant enhancement to both calcium and magnesium solubility at this phosphonate doping level.

On the other hand, when concentration of phosphates was increased to 558 mg/L, most results showed significant increase in the solubility of both calcium and magnesium.

The above confirmed that HEDP was by far the most effective candidate as a calcium and magnesium phosphonate complexing agent that was studied.

EXAMPLE 4

In a fourth study, the effects of heat-treatment (drying) process of BCC on the soluble calcium and magnesium were determined. The BCC for this study was freshly prepared in the lab and contained 1800 ppm calcium and 596 ppm magnesium on dry basis, respectively. In general, it was found that the solubility of calcium and magnesium is slightly higher from dissolving the dried BCCs than the wet ones. The results are listed in the table below.

| | Wet BCC | | DRY BCC | |
|---|---|---|---|---|
| HEDP, mg/L | Ca, mg/L | Mg, mg/L | Ca, mg/L | Mg, mg/L |
| 0 | 55.1 | 40.7 | 59.2 | 41.4 |
| 140 | 90.3 | 51.5 | 113.2 | 56.4 |
| 558 | 245 | 140 | 301 | 120 |

EXAMPLE 5

Prior studies demonstrated that phosphonates are effective calcium complexers for the production of low (calcium carbonate) residue CMC solutions. In this study, several other (groups of) candidates were investigated to evaluate their abilities to enhance the solubility of calcium in a CMC solution. These candidates were selected from compounds claimed to be effective in reducing hard water scaling problems in boilers as well as in other applications.

CMC (copper monoethanolamine carbonate) solutions for the experiments were from plant production and contained 9.5% copper, 32% MEA and with a pH of 9.3. In each experiment, about 100 mg of calcium (as $CaCl_2$) was added into 250 g of CMC solution (208 ml). After mixing well, this solution was further mixed with 200 ppm of each complexer candidate for 24 hours under good agitation. A sample solution was filtered with a 1.2 micron pore size GF/A glass fiber filter paper. The dissolved calcium in the CMC solution was determined by flame atomic absorption spectrometry (flame AA). The results of the experiments are listed in the table below.

| Experiment ID | Added Complexers | US Patent Reference | Dissolved Calcium, ppm |
|---|---|---|---|
| Control | None | Not applicable | 53.6 |
| 1 | 200 ppm Triglycolamic acid, 200 ppm Polyacrylamide[a] | U.S. Pat. No. 3,518,204 | 59.4 |
| 2 | 200 ppm Sodium monofluorophosphate | U.S. Pat. No. 5,182,028 | 58.0 |
| 3 | 200 pm Alginic acid | U.S. Pat. No. 6,641,740 | 63.0 |
| 4 | 200 ppm 2-Phosphonobutane-1,2,4-tricarboxylic acid, 200 ppm Quad-polymer[b] | U.S. Pat. No. 6,645,384 | 67.8 |
| 5 | 200 ppm Hydroxyethylidene-diphosphonic acid, 200 ppm Quad-polymer | | 86.3 |
| 6 | 200 ppm Hydroxyethylidene-diphosphonic acid | | 84.1 |

[a]CALLAWAY ® 4030;
[b]CL4800 (Chemtreat, Inc.)

The results above indicate that Hydroxyethylene-diphosphonic acid (HEDP) outperformed all other candidates for its ability to complex calcium ions. The addition of surfactants seemed to have limited effects on the calcium solubility in the CMC sample studied. This may be due to the fact that they functioned only as dispersants for the anti-scaling applications.

The examples and phosphonate inhibitors described herein are only exemplary. Numerous phosphonate inhibitors are known, including, just for example, aceto-diphosphonic acid, which would be very useful in this invention.

What is claimed is:

1. A method of preserving wood comprising:
   contacting wood with an aqueous solution of a wood preservative composition comprising
   copper-amine complex;
   one or more alkaline earth metal ions; and
   a precipitation inhibitor selected from hydroxyethylidene-diphosphonic acid (HEDP) or a salt thereof;
   2-phosphonobutane-1,2,4-tricarboxylic acid (PBTC) or a salt thereof;
   a compound having a plurality of phosphonate moieties, wherein the phosphorus atoms of the phosphonate moieties are separated by at least two carbon atoms, wherein the at least two carbon atoms are not linked to nitrogen atoms;
   a compound having at least one phosphonate moiety and one or more carboxylate moieties, wherein the phosphorus atom of the at least one phosphonate moiety and the one or more carboxylate moieties are separated by at least two carbon atoms; and mixtures thereof.

2. The method of claim 1, wherein the copper-amine complex is selected from a copper-ammonia complex, a copper monoethanolainine complex, a copper-diethanolamine complex, a copper-isopropanolamine complex, a copper-ethylenediamine complex and mixtures thereof.

3. The method of claim 1, wherein the alkaline earth metal ion is selected from calcium, magnesium, strontium and mixtures thereof.

4. The method of claim 1, wherein the molar ratio of the precipitation inhibitor(s) to the total alkaline earth metal ions is from about 1:3 to about 4:1.

5. The method of claim 1, wherein the precipitation inhibitor is HEDP or a salt thereof.

6. The method of claim 1, wherein the precipitation inhibitor is PBTC or a salt thereof.

7. The method of claim 5, wherein the concentration of the HEDP in the aqueous solution of the wood preservative composition is at least about 20 mg/L.

8. The method of claim 1, wherein the wood preservative composition further comprises one or more organic biocides.

9. The method of claim 1, wherein the aqueous solution of the wood preservative composition is prepared by diluting concentrate of the wood preservative composition with at least 2 volumes of water, wherein the concentrate comprises from about 20 to about 100 mmoles/L of the precipitation inhibitor.

10. The method of claim 1, wherein the aqueous solution of the wood preservative composition is prepared by diluting concentrate of the wood preservative solution with at least 2 volumes of water, wherein the concentrate comprises from about 10 to about 50 mmoles/L of the precipitation inhibitor.

11. A wood preservative comprising:
   an aqueous solution of a copper salt, copper complex, or a mixture thereof;
   one or more alkaline earth metal ions; and
   hydroxyethylidene-diphosphonic acid (HEDP) or a salt thereof.

12. The wood preservative of claim 11, wherein the ratio of moles of HEDP to kg of alkaline earth metal ions is from about 0.1 to about 4.

13. The wood preservative of claim 12, wherein the ratio of moles of HEDP to kg of alkaline earth metal ions is from about 0.2 to about 1.

14. The wood preservative of claim 11, wherein the ratio of HEDP to total alkaline earth metal ions is from about 0.3 mmoles/L to about 0.5 mmoles/L.

15. A wood preservative comprising:
   an aqueous solution of a copper salt, copper complex, or a mixture thereof;
   one or more alkaline earth metal ions; and
   a precipitation inhibitor having at least one phosphonate moiety and one or more carboxylate moieties, wherein the phosphorus atom of the at least one phosphonate moiety and the one or more carboxylate moieties are separated by at least two carbon atoms.

16. A wood preservative comprising:
   an aqueous solution of a copper salt, copper complex, or a mixture thereof;
   one or more alkaline earth metal ions; and a precipitation inhibitor having a plurality of phosphonate moieties, wherein the phosphorus atoms of the phosphonate moieties are separated by at least two carbon atoms, wherein the at least two carbon atoms are not linked to nitrogen atoms.

17. The wood preservative of any one of claims 11, 15 and 16, wherein the copper salt is copper carbonate, basic copper carbonate or mixtures thereof.

* * * * *